(12) United States Patent
McKay

(10) Patent No.: US 8,147,495 B2
(45) Date of Patent: Apr. 3, 2012

(54) METHODS AND KITS FOR TREATING FRACTURES WITH A BIOLOGICAL AGENT

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1479 days.

(21) Appl. No.: 11/623,605

(22) Filed: Jan. 16, 2007

(65) Prior Publication Data

US 2010/0256643 A1    Oct. 7, 2010

(51) Int. Cl.
    *A61F 2/46*    (2006.01)
(52) U.S. Cl. ........................................ 606/86 R
(58) Field of Classification Search ............... 606/86 R, 606/92–94
    See application file for complete search history.

(56) References Cited

U.S. PATENT DOCUMENTS

| | | | |
|---|---|---|---|
| 4,341,206 A * | 7/1982 | Perrett et al. ................... 606/80 |
| 4,969,888 A * | 11/1990 | Scholten et al. ................. 606/94 |
| 5,514,137 A * | 5/1996 | Coutts ............................ 606/62 |
| 6,179,826 B1 | 1/2001 | Aebischer et al. | |
| 6,241,734 B1 * | 6/2001 | Scribner et al. ................. 606/93 |
| 6,375,659 B1 * | 4/2002 | Erbe et al. ...................... 606/94 |
| 6,832,988 B2 | 12/2004 | Sproul | |
| 7,166,133 B2 * | 1/2007 | Evans et al. ................. 623/23.51 |
| 7,485,119 B2 * | 2/2009 | Thelen et al. .................... 606/63 |
| 7,736,381 B2 * | 6/2010 | Biedermann et al. .......... 606/301 |
| 7,938,835 B2 * | 5/2011 | Boucher et al. .................. 606/93 |
| 2005/0267483 A1 | 12/2005 | Middleton | |
| 2005/0277936 A1 | 12/2005 | Siravo et al. | |

\* cited by examiner

*Primary Examiner* — Anu Ramana (57) ABSTRACT

A method and kit for treating fractures in a subject entailing placing a temporary fixation device containing a wire in a percutaneous manner across a fracture line, drilling across the fracture line and delivering a biological agent. The biological device is delivered through an injection device which may be the same as the drilling device or different therefrom. The biological agent is delivered uniformly across the complete fractured bone and to the contralateral surface of the fractured bone through an injection device. The method may comprise additional steps of sliding a cannula over the fixation device and affixing the cannula to an outer surface of the fracture. In this embodiment, the drilling device, and later the injection device are placed within the cannula.

34 Claims, 4 Drawing Sheets

METHODS AND KITS FOR TREATING FRACTURES WITH A BIOLOGICAL AGENT

FIELD OF THE INVENTION

The present invention relates to a method of treating fractures in a subject percutaneously by drilling across the fracture line to deliver a biological agent uniformly across the complete fracture and to the contralateral surface. This can be achieved by either drilling across the fracture line with a cannulated drill or trocar needle and injecting the biologic agent through the drill itself, or by placing a temporary internal fixation device wire and drilling across the fracture line to deliver a biological agent. Alternatively, a cannula is placed over K-wires and/or Steinman pins and is optionally affixed to an outer surface of the fracture, a drilling device is inserted through the cannula, and the pathway is drilled across the fracture line with a drill or burr. A biological agent is delivered uniformly across the complete fractured bone and to the contralateral surface through the drilled area with an injection device placed within the cannula.

BACKGROUND OF THE INVENTION

Fractures are among the most common orthopedic problems, with about 6.8 million people needing medical attention each year in the United States. The average citizen in a developed country can expect to sustain two fractures over the course of his or her lifetime.

New methods of fixation for scaphoid fractures represent the most dramatic revolution in the treatment of wrist injuries in the last three decades. Fractures of the scaphoid usually occur in sporting accidents or during a fall on the outstretched hand. The scaphoid has a peculiar blood supply that renders it vulnerable to delayed healing or even failure to unite. Delayed or incomplete treatment can lead to complications such as severe wrist arthritis. Healing of fractures usually takes time and external fixation is required to hold the broken bones in place. Three to four month casting period that is necessary for healing can be quite disruptive to occupational and daily activities. Surgical treatment with percutaneous methods enables rapid healing without the confinement of a cast.

Attempts have been made to deliver biological agents to treat closed fractures and reduce the healing time. However, these biological agents are injected percutaneously to only one side of the outer surface of the fracture. This means that approximately three quarters of the fracture receives none or very little amount of a biological agent which could result in an ineffective clinical treatment. Delivery of the biological agents to such surfaces of the fracture and the complete circumference of the fracture line is required for effective therapy. Such treatment enhances the fracture healing and is desired.

In U.S. Pat. No. 6,179,826 to Aebischer et. al., implantable therapy systems were disclosed for controlled delivery of biological agents to the brain, spinal cord using a cannula. In U.S. Pat. No. 6,832,988 to M. E. Sproul, a surgical kit for inserting biological agent into a skeletal bone with a cannula is disclosed.

Nevertheless, there is a need in improvements of methods for treating fractures that provide for the biological agents to be distributed more uniformly across the fractured bone including the contralateral (usually the inner) surface of the fracture, and the perimeter of the fracture to promote healing.

SUMMARY OF THE INVENTION

The invention addresses drawbacks of the prior art by providing, in one aspect, a method for treating a fracture in a subject comprising: drilling across the fracture line with a drilling device; and delivering a biologic agent across the complete fractured bone through the drilling device. In one embodiment, the injection device contains one or, preferably, more, holes for dispensing the biologic agent.

In one embodiment, the biological agent comprises a BMP, a statin, or a combination thereof. In a preferred embodiment, the biological agent is delivered uniformly throughout the fractured surface.

In another aspect, the invention provides a method for treating a fracture in a subject comprising: placing a temporary internal fixation device in a percutaneous manner across a fracture line; placing a cannula over the fixation device; drilling across the fracture line with a drilling device; and delivering a biological agent across the fractured bone through an injection device placed within the cannula. In one embodiment, the injection device contains one or, preferably, more, holes for dispensing the biologic agent. Further, in one embodiment, the drilling device serves as an injection device.

In one embodiment, the biological agent comprises a BMP, a statin, or a combination thereof. In a preferred embodiment, the biological agent is delivered uniformly throughout the fractured surface.

In yet another aspect, the invention provides a kit for treating fractures in a subject comprising: a drilling device; and a biological agent. In one embodiment, the biological agent is delivered to a surface of a fractured bone in the subject through the drilling device.

In another embodiment, the kit further comprises a temporary internal fixation device; and a cannula having a diameter allowing said cannula to be placed over the temporary internal fixation device.

In another embodiment, the kit further comprises an injection device having a diameter allowing said injection device to be placed within the cannula.

In yet another embodiments of this aspect of the invention, the biological agent comprises a BMP, a statin, or a combination thereof.

BRIEF DESCRIPTION OF THE FIGURES

FIG. 6 shows drilling devices (a) a flexible burr; and (b) a multilumen or multiprobe needle.

FIG. 7 shows (a) a cannulated drill with holes; and (b) a trocar needle with holes.

DETAILED DESCRIPTION OF THE INVENTION

Figure 1:
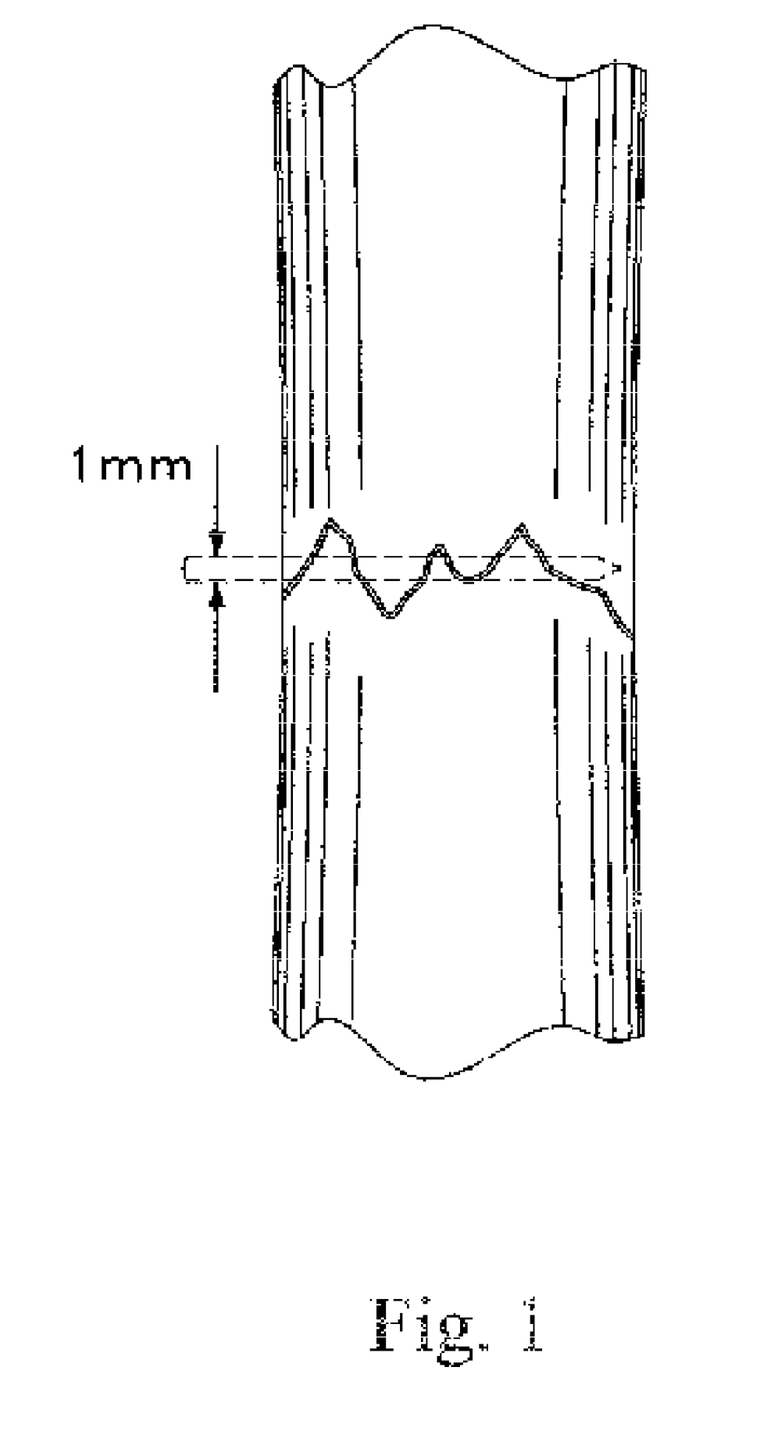
FIG. 1 shows a Steinman pin placed across the fracture line.
Figure 2:
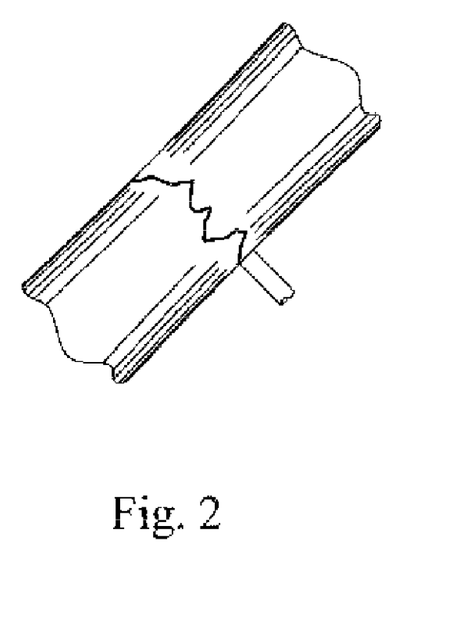
FIG. 2 shows a cannula placed on the fracture surface.
Figure 3:
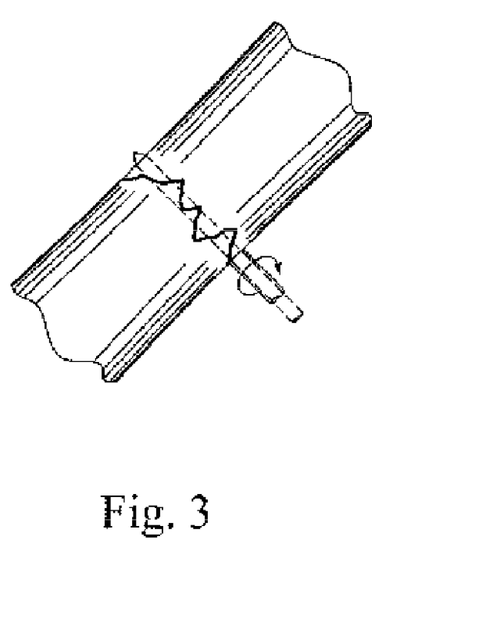
FIG. 3 shows a drilling device that is inserted within the inner bore of the cannula and shows the drilled path across the fracture line.
Figure 4:
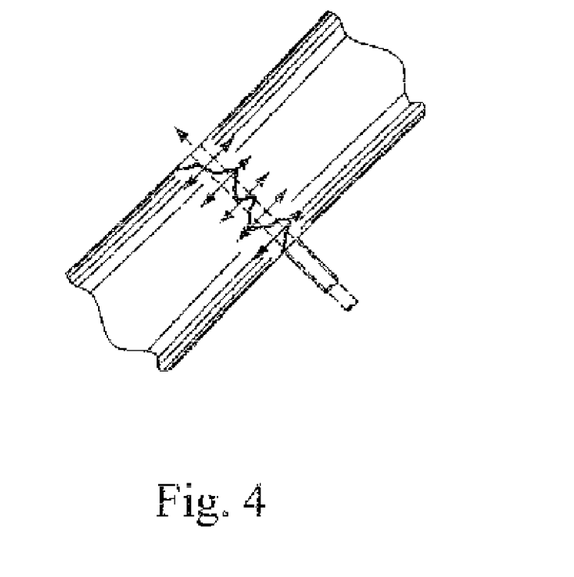
FIG. 4 shows the injection of the biological agent across the fracture line. The arrows indicate the direction of the dispersed biological agent.
Figure 5:
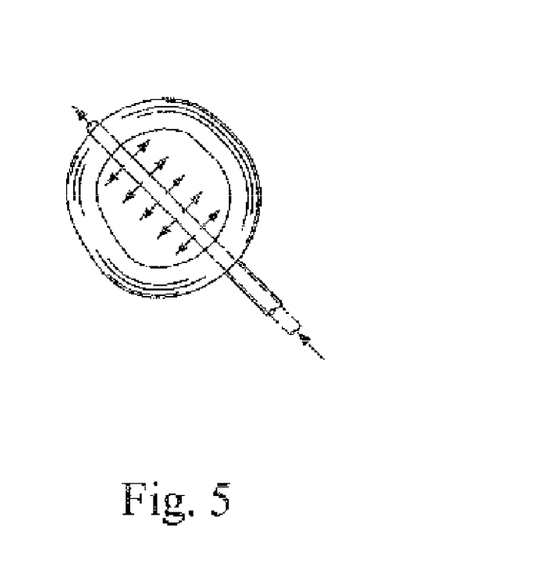
FIG. 5 shows a cross-sectional view of the fracture surface with the drilling device inserted. The arrows indicate the direction of the dispersed biological agent.
Figure 6A:
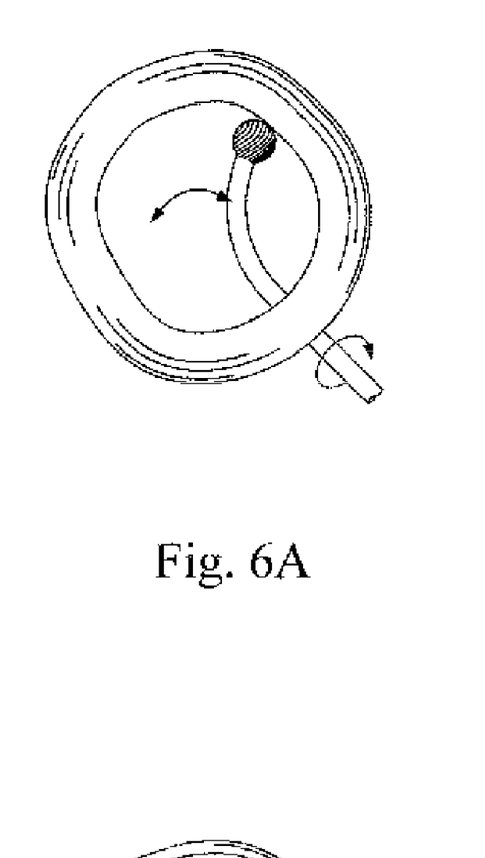
Figure 6B:
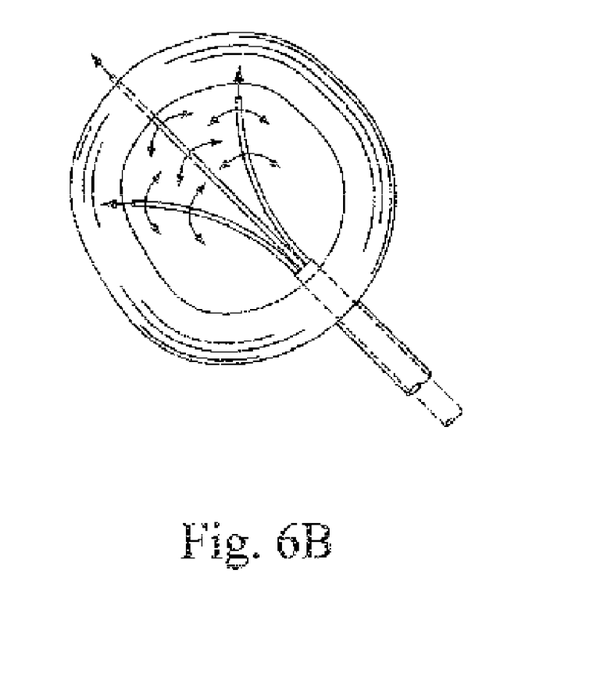
Figure 7A:
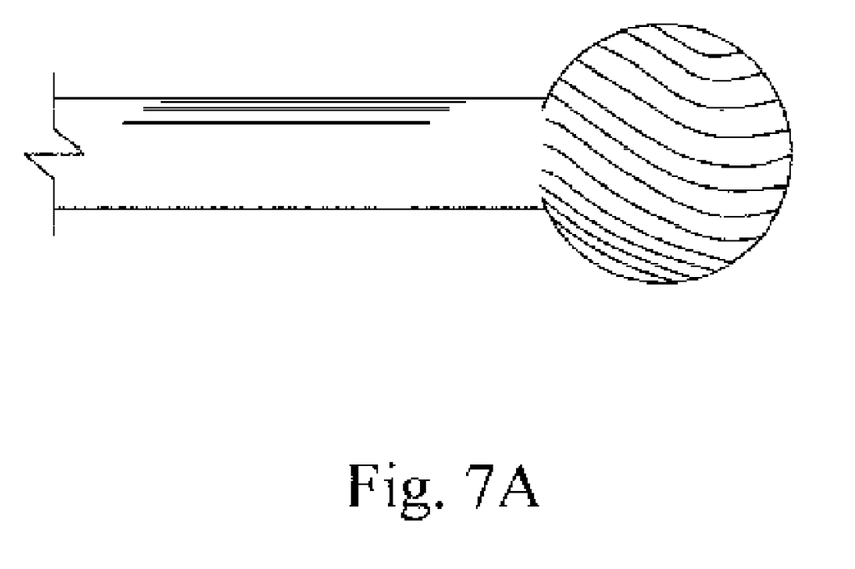
Figure 7B:
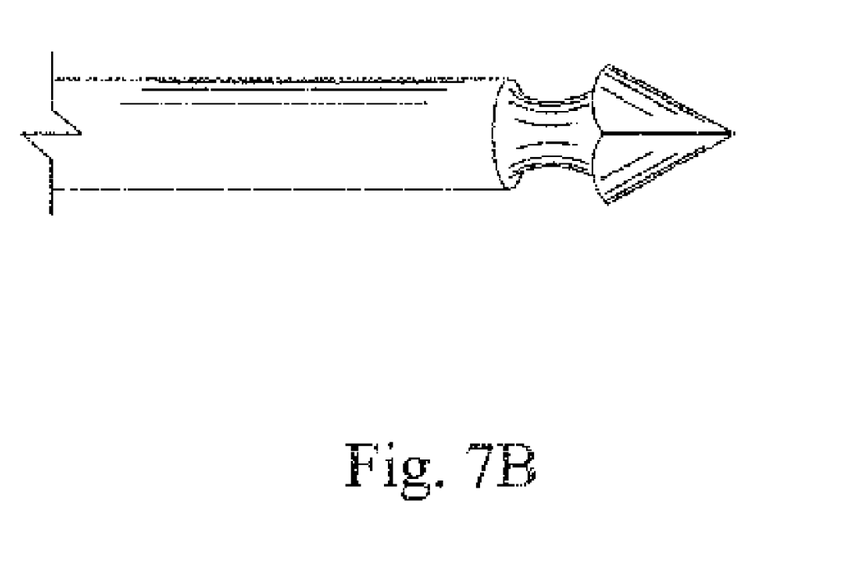

Unless defined otherwise, all technical and scientific terms used herein have the same meaning as is commonly understood by one of skill in the art to which this invention belongs. All publications and patents referred to herein are incorporated by reference.

Definitions

To aid in the understanding of the invention, the following non-limiting definitions are provided:

The term "fracture" refers to a disruption in the integrity of a living bone involving injury to bone marrow, periosteum, and adjacent soft tissues. Many types of fractures exist such as, for example, pathological, stress, non-union, delayed-union, and greenstick fractures. A fracture includes open and closed fractures.

The term "fracture line" refers to the line across where disruption of the integrity of the living bone has occurred.

The term "non-union" fracture refers to the fractures which are not completely healed nine months after the initial fracture. These are commonly found in clavicle fractures that are not healed usually within three months, and are usually painful and require surgical fixation.

The term "delayed-union" refers to a fracture that has not healed at least about six months post injury.

The term "affixing" means affixing, placing, suspending, telescoping, and docking.

The term "contralateral surface" means in the other surface, or opposite surface. Thus, for a bone if the treatment is applied to the outer surface, the inner surface is the contralateral surface.

The term "percutaneous placement" refers to minimally invasive technique of placing cannulae.

The term "cannula" refers to a flexible tube which when inserted into the body is used either to withdraw fluid or insert medication. Cannula normally comes with a "trocar needle (a sharp pointed needle) attached which allows puncture of the tissues and bone to gain access into the desired space.

The term "injection device" refers to a tool inserted within the cannula and which is used to deliver the biological agent.

The term "drilling" device refers to a tool inserted within the cannula and is used to drill the bone and the soft tissue.

The term "soft tissue" refers to tissues that connect, support, or surround the bone and organs of the body.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The term "subject" includes a living or cultured system upon which the methods and/or kits of the current invention is used. The term includes, without limitation, humans.

The term "practitioner" means a person who practices methods, kits, and compositions of the instant invention on the subject. The term includes, without limitations, doctors, other medical personnel, and researchers.

The term "biological agent" refers to a substance that is made from a living organism or its products and is used in the prevention, diagnosis, or treatment of diseases and fractures. Thus, the term "biological agent" includes, without limitations, antibodies, interleukins, growth factors, antibiotics, anti-inflammatory agents, analgesics, vaccines, and any combinations thereof.

The terms "uniform" and "uniformly" in application to the delivery of the biological agent refer to a distribution of the biological agent across the surface of the fracture, wherein at least 50% of the surfaces of the fracture has access to a therapeutic level of the content of the biological agent delivered. In different embodiments, at least 60% or at least 70% or at least 80% or at least 90% or at least 95% or 100% of the surfaces of the fracture has access to the therapeutic level of the content of the biological agent delivered.

The term "temporary" in application to placement of the fixation device refers to placement of the fixation device for a time of drilling across the fracture bone and delivery of the biological agent, and removal of the fixation device thereafter.

All references to chemical compounds, including biological agents, without limitation their form (i.e., salts, esters, hydrates, etc.), wherein said forms possess at least partial activities of the respective chemical compounds.

Advantages of the present invention over the prior art is that it provides for a more uniform distribution of the biological agent introduced percutaneously in the vicinity of the fracture line in a closed or open fracture to reduce the time for bone healing. It is a less invasive method to treat a delayed or non-union fracture. The drilling step provides for new bleeding in the bone and facilitates healing in combination with the injected biological agent.

Fractures

A fracture is a break of a bone and is described by its appearance on X-rays. In a long bone of any limb, common for most fractures, a transverse fracture occurs when the fracture line is transverse across the shaft of the bone which is perpendicular to the long axis of the bone. This is usually a result of a bending injury. An oblique fracture occurs when the fracture line is oblique across the shaft of the bone, usually a result of a combination bending and twisting injury. A spiral fracture occurs when the fracture line spirals around the shaft of the bone, a result of a pure twisting injury. A comminuted fracture occurs when the bone is broken into more than two fragments.

If the fracture fragments are in good position, the fracture is called an undisplaced fracture. Sometimes the fracture line is so fine that it is called a hairline fracture. If there is displacement of the fracture fragments, it is called a displaced fracture. A displaced fracture may be axially displaced, angulated or rotated.

With severe trauma, a disruption of the muscles and skin may occur, causing the fracture to communicate with the external environment and is referred to as an open or compound fracture. Most fractures do not communicate with the external environment because the skin is not broken and is referred to as a closed fracture. Typically in closed or simple fractures the bone is broken, but the skin is not lacerated.

In open or compound fractures the skin may be lacerated by the bone or by a blow that breaks the skin at the time of the fracture. The bone may or may not be visible in the wound.

A stress fracture occurs when a bone is subject to repeated stress, e.g., from running or marching. This is also called a fatigue fracture.

A pathological fracture occurs when minor stress is placed upon a bone that is weakened by pre-existing disease, e.g., bone affected by osteoporosis, or a bone cyst, or cancer cells.

An avulsion fracture occurs when a muscle-tendon unit exerts such traction force on the bone it is attached to, that it avulses off a piece of bone. This is more frequent in children and adolescents where the muscle-tendon unit is stronger than the bone. It happens typically around the hip and knee.

A greenstick fracture occurs in children, because of the increased elasticity of young bones. The fracture is an incomplete fracture that goes partly through the bone, leaving part of the cortex and periosteum (covering) of the bone intact. If a compressive force is applied on a child's bone, e.g., when he falls on the outstretched hand, it buckles the bone just above the wrist, giving an expanded appearance on X-rays. This is a type of greenstick fracture, called a buckle fracture or torus fracture.

Types of fractures that could be treated in the present invention include for example wrist fractures, neck fractures, arm fractures, leg fractures, foot fractures, ankle fractures, hand fractures, hip fractures, spinal fractures, clavical fractures, high risk or potential slow healing fractures, delayed-union fractures, and non-union fractures.

Fractures can be stabilized by internal fixation and with adequately securing the fracture site and resulting in a reduction of the fracture. Once a reduction is achieved, the fracture is stabilized and maintained.

Many techniques of surgical fixation of distal clavicle fractures have been described in the literature. Treatment of such fractures requires direct visualization and reduction of the fracture fragments through a vertical incision. Stable fracture fixation can be achieved in many ways, including combinations of a coracoclavicular screw, Dacron or Mersilene tape, tension banding, Kirschner wire (K-wire), and clavicular plates. Regardless of the exact technique used, the general principles of fracture reduction and fixation and stabilization of the coracoclavicular interval apply. Steinman pins have also been used in internal fixation of structures.

Percutaneous Surgery

Percutaneous surgery is based on needle and guidewire access to organs or to bone. Once such guidewire access is obtained, various catheters can be placed into the bone or organs for drainage of fluids and/or to facilitate delivery of therapeutics.

The Seldinger technique, a medical procedure to obtain safe access to blood vessels and other hollow organs is commonly used in angiography, insertion of chest drains and central venous catheters, insertion of percutaneous endoscopic gastrostomy tubes, and numerous other interventional medical procedures. Such a procedure could be used in the present invention.

During percutaneous procedures, the practitioner performs surgery by inserting instruments or fracture fixation devices directly through the skin, and monitors the accurate placement of these devices with x-rays or fluoroscopy. For example, diagnosis of scaphoid fractures has been improved with the use of advanced imaging methods. Images obtained with fluoroscopy is then used to guide the insertion of fixation devices such as screws, usually through a 1 to 2 mm incision, into the bone to stabilize it. An advantage of percutaneous surgery is that surgery is completed in less than an hour. In the past, an open procedure was required and the patient then wore a cast for up to 2 or 3 months postoperatively. Once the fixation is complete, the patient is generally able to recover while wearing only a removable splint, and is able to begin range of motion exercises almost immediately after surgery.

Several fractures may now be treated using percutaneous fixation techniques, including those of the phalanges and metacarpals. For severe fractures involving the finger joints, the patient's finger is sometimes placed in an external fixator apparatus, and the practitioner employs fluoroscopy to guide the placement of wires and screws for bone stabilization. Advantage of this treatment is the ability to allow the patient to begin gentle motion within a few days of surgery. Early rehabilitation of these complex injuries has been shown to decrease the occurrence of post-operative joint stiffness when compared with traditional open techniques.

The present invention can be used to treat soft tissue injuries. Percutaneous procedures can be used for soft tissue procedures. Percutaneous procedures for soft tissue injuries include, without limitation, treatment for trigger finger, a condition in which a tendon becomes entrapped within a tight sheath in the palm, and painfully snaps during routine use of the hand. Release is provided by dividing the stenotic sheath. In traditional surgery, this procedure requires an open incision in the palm of the hand. Percutaneous techniques allow the surgeon to accomplish the same surgical result without an incision, using a special needle. Injection of a radiocontrast agent may be used to visualize organs. Interventional procedures, such as thermoablation, angioplasty, embolisation or biopsy, may be performed.

Kirschner Wires

Kirschner wires, or K-wires, are used for temporary and definitive treatment of fractures. A K-wire is a thin, rigid wire that can be used to stabilize bone fragments and are drilled through the bone to hold the fragments in place. They are placed percutaneously (usually through the skin), thus avoiding an operation in some cases. In other cases, the K-wires are used after an operation to hold bone fragments in place. K-wires resist only changes in alignment. They do not resist rotation and have poor resistance to torque and bending forces. They are commonly used as adjunctive fixation for screws or plates and screws especially involving fractures around joints.

When K-wires are used as the sole form of fixation, casting or splinting is used in conjunction. K-wire fixation have been found adequate for small fragments in metaphyseal and epiphyseal regions, especially in fractures of the distal foot, wrist, and hand, such as Colles fractures, and in displaced metacarpal and phalangeal fractures after closed reduction. K-wires are commonly used as adjunctive therapy for many fractures such as patellar fractures, proximal humerus fractures, olecranon fractures, and calcaneus fractures.

K-wires or Steinman pins are sterilized, sharpened, smooth stainless steel pins used in orthopaedics and other types of medical and veterinary surgery. They come in different sizes and are used to hold bone fragments together (pin fixation) or to provide an anchor for skeletal traction. Steinman pins and K-wires are often driven into the bone through the skin (percutaneous pin fixation) using a power or hand drill. Fluoroscopy may be used to confirm the position of the K-wire and to maneuver it to the desired location.

Cannula

Cannula is a hollow tube which is used to protect surrounding soft tissues in the treatment of distant bone structures when inserted into the body. Cannulae normally come with a trocar needle, usually a sharp pointed needle attached which allows a puncture of the body to get into the intended space. The present invention may use an internal docking wire to guide the cannula to a desired location. The diameter and length of the cannula is selected by the practitioner depending on the fracture to be treated and access to the fracture line. As an example a rigid cannula can be used in the present invention.

Drilling Device

The drilling devices of the present invention include straight rigid drills, straight rigid burrs, flexible burrs, steerable burrs and needles. Any sharp pointed needle or a trocar needle that can be inserted within the cannula may comprise the drilling device of the present invention. The drilling device may contain holes along the hollow shaft to inject the biological material during or after drilling.

In an embodiment, the drilling device comprises a cannulated drill having cutting flutes at the leading edge and the rest of the smooth shaft with holes on the side of the shaft to inject biologic agent.

In a set of embodiments, the drilling device is also used as an injection device. For example, in one embodiment, the drill contains an internal shaft that can be removed after drilling across the fracture line and the biologic agent injected into the hollow drill and out the side holes.

In an embodiment the drilling can be done with ultrasound. Such ultrasound drilling procedures are disclosed in U.S. Pat. No. 6,832,988. In additional embodiments, the drilling device may use electric power or the drilling device may be used for manual drilling.

Any design that facilitates the use of a flexible burr which provides for access to contralateral surface of the fracture may also be employed in the present invention. Such a flexible burr may provide for the drilled pathways to reach the internal surfaces of the medulary canal and opposing fracture surfaces. Also, the use of a multi-lumen tubing or multi-probed needle facilitates uniform distribution of the biological agent across the fracture line. Multi-lumen tubing may have several diameters and radiate out in several directions. An advantage of using such a multiprobed needle is that the surface area covered by distributed biological agent is increased.

Biological Agent

For a faster healing, it may be desirable to administer a biological agent. In one embodiment, the biological agent comprises a protein, a fragment of a protein, a nucleic acid sequence, a small molecule, a cell, or a combination thereof.

Non-limiting examples of suitable cell types include mesenchymal stems cells, pluripotent stem cells, embryonic stem cells, osteoprogentior cells, bone marrow cells, osteoblasts and osteoclasts. A person of the ordinary skill in the art will appreciate that the cells may be derived from autogeneic, allogeneic or xenogeneic source. In the most preferable embodiment, the suitable cells are derived from an autogeneic source (i.e., from the patient him- or herself). The cells may also be modified, for example, by transfection with a nucleic acid sequence encoding a molecule of choice, e.g., a Bone Morphogenic Protein or a LIM Mineralization Protein.

Growth factors suitable for use in the present invention include but are not limited to bone morphogenic proteins, for example, BMP-2, rhBMP-2, BMP-4, rhBMP-4, BMP-6, rhBMP-6, BMP-7, rhBMP-7, GDF-5, and rhGDF-5, as disclosed, for example, in the U.S. Pat. Nos. 4,877,864; 5,013, 649; 5,661,007; 5,688,678; 6,177,406; 6,432,919; 6,534,268, and 6,858,431, and in Wozney, J. M., et al. (1988) *Science*, 242(4885):1528-1534. BMP's have been shown to be excellent at growing bone and there are several products being tested. For example, rhBMP-2 delivered on an absorbable collagen sponge (INFUSE® Bone Graft, Medtronic Sofamor Danek, Memphis, Tenn.) has been used inside titanium fusion cages and resulted in fusion in 11 out of 11 patients in a pilot study and 99% of over 250 patients in a pivotal study. In July, 2002 INFUSE® Bone Graft received FDA approval for use in certain types of spine fusion. A pilot study with BMP-2 delivered on a ceramic carrier was recently published and reported a 100% successful posterolateral fusion rate. BMP-7 (OP-1) has reported 50-70% successful posterolateral lumbar fusion results in human studies to date. On May 4, 2004, INFUSE® Bone Graft was approved for acute, open fractures of the tibial shaft (Bosse et al. *NEJM* 347(24): 1924-1931, 2002; Govender et al. *JBJS* 84(12): 2123-2134, 2002).

Additionally, suitable growth factors include, without limitation, statins, Nell-1 protein, LIM mineralization protein, platelet derived growth factor (PDGF), transforming growth factor B (TGF-B), insulin-related growth factor-I (IGF-I), insulin-related growth factor-II (IGF-II), fibroblast growth factor (FGF), beta-2-microglobulin (BDGF II), as disclosed in the U.S. Pat. No. 6,630,153.

Examples of stains include without limitation Cerivasttin, lovastatin, simvastatin and pravastatin, fluvastatin, rosuvastatin, atorvastatin, rivastatin, HMG CoA synthetase inhibitors (e.g., L-659,699 ((E,E)-11-[3'R-(hydroxy-methyl)-4'-oxo-2'R-oxetanyl]-3,5,7R-trimethyl-2,4-undecadienoic acid)), and any combinations thereof.

The present invention can also include, without limitation, biological agents such as free radical scavengers and chelators enzymes, co-enzymes, spin-trap agents, ion and metal chelators, lipid peroxidation inhibitors such as flavinoids, N-tert-butyl-alpha-phenylnitrone, NXY-059, Edaravone, glutathione and derivates, antibiotics, analgesic, and any combinations thereof.

The present invention can also include biological agents that are anti-inflammatory compounds both steroidal and non-steroidal. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds can also be used.

Non-limiting examples of non-steroidal anti-inflammatory compounds include nabumetone, celecoxib, etodolac, nimesulide, apasone, gold, oxicams, such as piroxicam, isoxicam, meloxicam, tenoxicam, sudoxicam, and CP-14,304; the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

The variety of compounds encompassed by the anti-inflammatory group of agents are well-known to those skilled in the art. For detailed disclosure of the chemical structure, synthesis, side effects, etc. of non-steroidal anti-inflammatory compounds, reference may be made to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974), each incorporated herein by reference. Mixtures of these non-steroidal anti-inflammatory compounds may also be employed, as well as the pharmacologically acceptable salts and esters of these compounds. Suitable antibiotics include, without limitation nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol or any combination thereof.

Suitable analgesics include, without limitation, non-steroid anti-inflammatory drugs, non-limiting examples of which have been recited above. Further, analgesics also include other types of compounds, such as, for example, opioids (such as, for example, morphine and naloxone), local anaesthetics (such as, for example, lidocaine), glutamate receptor antagonists, α-adrenoreceptor agonists, adenosine, canabinoids, cholinergic and GABA receptors agonists, and different neuropeptides. A detailed discussion of different analgesics is provided in Sawynok et al., (2003) *Pharmacological Reviews*, 55:1-20, the content of which is incorporated herein by reference.

The biological agent may also include a radiocontrast agent to verify the placement and/or the distribution of the biological agent in the target area. Suitable radiocontrast agents include barium and iodine compounds, metal ions, nitroxides, and gadolinium complexes, such as gadodiamine.

Methods

In one aspect, the methods of the instant invention involve drilling across the fracture line with the drilling device, and injecting the biological agent. In this aspect, the drilling device is also used as the injection device. Further, a person of the ordinary skill in the art will recognize that drilling devices which are especially advantageous for this aspect of the invention include drilling devices which have cutting flutes only at their respective distal ends and/or drilling devices which include the respective internal shafts which may be removed once the respective drilling devices are positioned for the uniform delivery of the biological agent.

In another aspect, the methods of the present invention further involve the temporary placement of K-wires and/or Steinman pins to stabilize the fracture. Such placement of the K-wires is done percutaneously as described above. In an embodiment K-wires are placed either proximal or distal to the fracture and gain firm anchorage in the proximal and distal metaphysic. Crossover of K-wires at the fracture line is not recommended by skilled artisans as rigid distraction of the fracture may occur. The placement of K-wires and/or Steinman pin across the fracture line may be achieved via fluoroscopic imaging.

In one embodiment of the methods of the instant invention, the drilling device comprises a hollow shaft and a distal end having cutting flutes. The outer diameter of the shaft of the drilling device is relatively small, e.g., no more than 5 mm, preferably about 2 mm. The tip of the drilling device should be sufficient to allow the penetration of the shaft of the drilling device into the drilled bone. For example, if the outer diameter of the shaft of the drilling device is 2 mm, then the tip of the drilling device should have an outer diameter of about 2.2 mm. The inner diameter of the shaft of the drilling device should be sufficiently large to allow the drilling device to slide over the fixation device, e.g., the Steinman pin. In an embodiment where no cannula is used, the manual drilling is preferred. If a cannula is used, then power drilling can also be performed. The Steinman pin will be occupying the internal diameter of the shaft of the drilling device, thus providing an advantage of preventing debris from getting into the shaft during the drilling procedure. Once the drilling is done, the Steinman pin is removed and an injection device, e.g., an injection tube, is inserted to inject the biological agent. A person of the ordinary skill in the art will appreciate that the external diameter of the injection tube should be small enough to allow the injection tube to slide into the shaft of the drilling device. In this exemplified embodiment, the inner diameter of the injection tube is about 0.8 mm. Optionally a distal end (the end which is not fed into the shaft of the drilling device) of the injection tube comprises a luer lock for easy attachment of a syringe with the biological agent. This technique eliminates the need for the cannula and minimizes the number of steps in the procedure.

In another set of embodiments, a cannula may be used. The cannula is guided over the K-wire or the Steinman pin to affix to the outer surface of the fracture. Such guiding includes telescoping of the cannula over the K-wire or the Steinman pin. In an another embodiment the cannula can be slid over the K-wire or the Steinman pin which serves as a guidewire into the vicinity of the fracture. In an embodiment a blunt cannula also referred to as a sheath can be used. If required an external vise could be used to hold the working cannula stationary during the procedure. The cannula may be modified to enhance the ability to cut through the bone, particularly if a biopsy is necessary.

Once the cannula is placed over the K-wire or the Steinman pin to the desired location at the surface of the bone, the drilling device is placed within the cannula over the Steinman pin or the K-wire. Optionally the cannula may be affixed to the bone surface. The cannula serves to protect the soft tissues during the drilling procedure. Accordingly, in this embodiment, power drilling may be used, but the manual drilling is also suitable. After the drilling is complete, the drilling device is removed from the cannula, leaving the Steinman pin in place. The cannula bore is now open for either removing material for biopsy, for creating a space, or for dispensing a biological agent for treatment.

In the next step, an injection device, e.g., a hollow tube for injecting the biological agent, is inserted over the Steinman pin. Thus, the diameter of the hollow tube should be sufficient to allow the, e.g., injection tube to slide over the Steinman pin. The Steinman pin is then removed. The distal end of the hollow tube can have a "luer lock" so that a syringe loaded with the biologic agent can be easily attached. This information needs to also be added to the application.

A drilling device with a straight or steerable burr maybe used to drill across the fracture line. A steerable burr has the advantage of adapting to the contours of the fracture line during drilling. In an embodiment a sharp cannula may be used to drill across the fracture line without the use of an external device.

In an embodiment an injection device is introduced through the same drilled hole(s) to inject the biological agent. Such an injection device is placed within the cannula. The drilled pathway allows for the biological agent to obtain adequate wetting of the contralateral surface of the fractured bone. Drilling devices may contain holes that serve to dispense the biological agent and serve as both drilling device and the injection device. In such an instance both drilling and injection can be done concurrently. Another embodiment entails drilling and injection may be performed concurrently using two devices.

In yet another embodiment the biological agent is injected and is in contact with around the complete circumference of the fracture line. The biological agent may leak out the fracture line indicating that coverage of the areas affected by the fracture is in contact with the injected biological agent. In a further embodiment the surface area may be completely wetted by the injected biological agent.

In an embodiment the uniform distribution of the biological agent significantly facilitate fracture repair leading to accelerated fracture healing time and higher overall healing rates.

In one embodiment, the biological agent is in a composition having a viscosity allowing it to flow into the cannula. Suitable viscosities include viscosities that allow adequate wetting of the fracture surface by the biological agent. The viscosity of the biological agent is such that the entire amount of the material is injected from the cannula. A plunger may be inserted into the cannula to inject the biological agent into the cancellous portion of the bone. The diameter of the plunger maybe slightly less than the inner diameter of the cannula. In this instance, the amount of biological agent delivered is precisely measured to be the corresponding volume of the cannula.

In another embodiment, low to medium viscosity biological agent delivered through the cannula at a low pressure, thus providing for effective dispersion for the biological agent. A pump providing said low pressure is especially suitable for this embodiment of the invention. In different embodiments of the invention, the pump may include, without limitations, an osmotic pump or an electromechanical pump.

The amount of biological agent may be adjusted to amount required to adequately wet the fracture surface area. This may be accomplished through the continued fluoroscopic observance of the procedure. If more material is necessary in a particular procedure, multiple injections of the biological agent may be performed.

When the appropriate amount of the biological agent has been injected into the bone, the injection device may be withdrawn. For example, the biological agent may be injected as a powder or granules and subsequently transformed into a liquid within the bone. The cannula is subsequently withdrawn from the bone. In another embodiment, a sealing device may be used to close the hole made by the procedure.

In an embodiment, the inner surface of the medulary canal can be decorticated to cause a bleeding bone bed which will further promote bone healing. In such a procedure the biological agent injected may help to promote healing by being transported with the blood.

In another embodiment, complications such as infection and compartment swelling may be avoided by using antibiotic agents, anti inflammatory agents, or non-steroidal anti-inflammatory compounds as the biological agent.

In another aspect, the fracture treatment system of this invention is in the form of a kit. Generally, the kit includes the drilling device and the biological agent. In one embodiment, the drilling device may be used as an injection device. In another embodiment, the kit includes an injection device which is separate from the drilling device, as described above.

In another embodiment, the kit includes a cannula. Cannulae used in the present invention include cannula with the appropriate size for the size fracture. Such cannula system is designed for percutaneous or direct visualization insertion and may be obtained from commercial suppliers, such as, for example, Medtronic Inc. Such kits may contain a cannula with introducer, stepped dilators, guide wire and scalpel blade. The cannulae of this and other embodiments of the kit should preferably have sufficiently large inner diameter to accommodate the drilling device and the injection device.

In an embodiment, the kit of the present invention may include a docking needle having an insertion point for penetration through the cutaneous layer of the patient. The insertion point passes through the skin, muscle and the hard shell of the bone into the softer cancellous bone material.

The needle is of a size and material to withstand the compression required for insertion without deformation. The needle may be made of stainless steel, other metals, alloys, or suitable polymers. Normally, the insertion is performed manually by axial pressure at the trailing end of the needle to include striking the needle with a surgical hammer.

In another embodiment, the kit further comprises a set of instructions. The set of instructions preferably comprises information for safe and efficient use of the kit. A person of the ordinary skill in the art will appreciate that the set of instructions may be provided in any form including, without limitations, written, electronic, audio-recorded, video-recorded, and any combination thereof.

The patent and scientific literature referred to herein establishes the knowledge that is available to those with skill in the art. All U.S. patents and published or unpublished U.S. patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the claims.

The invention claimed is:

1. A method for treating fractured bone in a subject, the fractured bone including a fracture surface that defines a fracture line disposed along the fracture surface, the method comprising the steps of:
   providing a drilling device that includes at least one opening defined in a side surface of the drilling device;
   drilling along the fracture line with the drilling device to create a drilled pathway along the fracture surface; and
   delivering a biological agent through the at least one opening of the drilling device across the fracture surface.

2. The method of claim 1 wherein the fracture is an open or closed fracture.

3. The method of claim 1 wherein the drilling device is selected from the group consisting of a straight burr, a steerable burr, a needle, and a trocar needle.

4. The method of claim 1 wherein the drilling device comprises a flexible burr.

5. The method of claim 1 wherein the drilling device includes a plurality of openings defined in the side surface of the drilling device for dispensing the biological agent.

6. The method of claim 1 wherein the drilling device serves as an injection device.

7. The method of claim 1 wherein the drilling across the fracture line is performed via fluoroscopic imaging.

8. The method of claim 1 further comprising an external vise.

9. The method of claim 1 wherein the biological agent comprises a growth factor selected from the group consisting of Bone Morphogenic Protein (BMP), Statins, Nell-1 protein, LIM mineralization protein, platelet derived growth factor (PDGF), transforming growth factor B (TGF-B), insulin-related growth factor-I (IGF-I), insulin-related growth factor-II (IGF-II), fibroblast growth factor (FGF) and beta-2-microglobulin (BDGF II).

10. The method of claim 9, wherein the biological agent is a statin.

11. The method of claim 1 wherein the biological agent comprises a Bone Morphogenic protein (BMP) selected from the group consisting of BMP-2, rhBMP-2, BMP-4, rhBMP-4, BMP-6, rhBMP-6, BMP-7, rhBMP-7, GDF-5, and rhGDF-5.

12. The method of claim 1 wherein the biological agent comprises a Bone Morphogenic protein (BMP) selected from the group consisting of BMP-2, rhBMP-2, BMP-4, rhBMP-4, BMP-6, rhBMP-6, BMP-7, rhBMP-7, GDF-5, and rhGDF-5.

13. The method of claim 12 wherein the Bone Morphogenic protein (BMP) is selected from group consisting of BMP-2 and rhBMP-2.

14. The method of claim 1, wherein the biological agent is delivered uniformly across the fracture surface.

15. The method of claim 1, wherein the fracture is a delayed fracture or a non-union fracture.

16. A method for treating fractured bone in a subject, the fractured bone including a fracture surface that defines a fracture line disposed along the fracture surface, the method comprising the steps of:
placing a temporary internal fixation device in a percutaneous manner across the fracture line;
placing a cannula over the fixation device;
drilling along the fracture line with a drilling device to create a drilled pathway along the fracture surface; and
delivering a biological agent across the fracture surface and a contralateral surface through an injection device placed within the cannula.

17. The method of claim 16, further comprising affixing the cannula to an outer surface of the bone.

18. The method of claim 16 wherein the fracture is a open or closed fracture.

19. The method of claim 16 wherein the temporary internal fixation device comprises a K-wire, Steinman pin, or a combination thereof.

20. The method of claim 16 wherein the drilling device is selected from the group consisting of a straight burr, a steerable burr, a needle, and a trocar needle.

21. The method of claim 16 wherein the injection device may be selected from a multilumen tubing, a multiprobe needle or a syringe.

22. The method of claim 16 wherein the injection device contains holes for dispensing the biologic agent.

23. The method of claim 16 wherein the drilling device serves as an injection device.

24. The method of claim 16 wherein the cannula protects the soft tissue during drilling.

25. The method of claim 16 wherein the placing of temporary fixation device in percutaneous manner across the fracture line is performed via fluoroscopic imaging.

26. The method of claim 16 wherein the drilling device comprises a flexible burr.

27. The method of claim 16 further comprising an external vise.

28. The method of claim 16, wherein the biological agent is delivered via a pump.

29. The method of claim 16 wherein the biological agent comprises a growth factor selected from the group consisting of Bone Morphogenic Protein (BMP), Statins, Nell-1 protein, LIM mineralization protein, platelet derived growth factor (PDGF), transforming growth factor B (TGF-B), insulin-related growth factor-I (IGF-I), insulin-related growth factor-II (IGF-II), fibroblast growth factor (FGF) and beta-2-microglobulin (BDGF II).

30. The method of claim 29, wherein the biological agent is a statin.

31. The method of claim 16 wherein the biological agent comprises a Bone Morphogenic protein (BMP) selected from the group consisting of BMP-2, rhBMP-2, BMP-4, rhBMP-4, BMP-6, rhBMP-6, BMP-7, rhBMP-7, GDF-5, and rhGDF-5.

32. The method of claim 31 wherein the Bone Morphogenic protein (BMP) is selected from group consisting of BMP-2 and rhBMP-2.

33. The method of claim 16, wherein the delivery of the biological agent across the fractured surface is uniform.

34. The method of claim 16, wherein the fracture is a delayed fracture or a non-uniform fracture.

* * * * *

UNITED STATES PATENT AND TRADEMARK OFFICE
CERTIFICATE OF CORRECTION

PATENT NO. : 8,147,495 B2
APPLICATION NO. : 11/623605
DATED : April 3, 2012
INVENTOR(S) : McKay It is certified that error appears in the above-identified patent and that said Letters Patent is hereby corrected as shown below:

In Column 1, Line 10, delete "biologic" and insert -- biological --, therefor at each occurrence throughout the patent.

In Column 1, Line 52, delete "et. al.," and insert -- et al., --, therefor.

In Column 5, Line 7, delete "clavical" and insert -- clavicle --, therefor.

In Column 7, Line 13, delete "medulary" and insert -- medullary --, therefor.

In Column 7, Line 27, delete "osteoprogentior" and insert -- osteoprogenitor --, therefor.

In Column 7, Line 66, delete "Cerivasttin," and insert -- Cerivastatin, --, therefor.

In Column 8, Line 8, delete "flavinoids," and insert -- flavonoids, --, therefor.

In Column 9, Line 17, delete "lincomycirl," and insert -- lincomycin, --, therefor.

In Column 9, Lines 22-23, delete "rolitetracyclin," and insert -- rolitetracycline, --, therefor.

In Column 9, Line 25, delete "sulfadiazin," and insert -- sulfadiazine, --, therefor.

In Column 9, Line 38, delete "canabinoids," and insert -- cannabinoids, --, therefor.

In Column 11, Line 59, delete "medulary" and insert -- medullary --, therefor.

Signed and Sealed this
Seventh Day of August, 2012

David J. Kappos
*Director of the United States Patent and Trademark Office*